United States Patent
Faulks et al.

[19]

[11] Patent Number: 6,117,121
[45] Date of Patent: *Sep. 12, 2000

[54] ABSORBENT ARTICLE USING EXTENSIBLE LEG CUFFS

[75] Inventors: Michael John Faulks, Neenah; Thomas Walter Odorzynski, Green Bay; Paul John Serbiak; Alan Francis Schleinz, both of Appleton; Daniel Robert Schlinz, Greenville, all of Wis.

[73] Assignee: Kimberly-Clark Worldwide, Inc., Neenah, Wis.

[ * ] Notice: This patent issued on a continued prosecution application filed under 37 CFR 1.53(d), and is subject to the twenty year patent term provisions of 35 U.S.C. 154(a)(2).

[21] Appl. No.: 08/570,052

[22] Filed: Dec. 11, 1995

[51] Int. Cl.$^7$ .................................................. A61F 13/15
[52] U.S. Cl. ..................................... 604/385.2; 604/385.1
[58] Field of Search .................................. 604/358, 378, 604/385.1, 385.2, 383, 373

[56] References Cited

U.S. PATENT DOCUMENTS

| | | | |
|---|---|---|---|
| 2,969,065 | 1/1961 | Farnsworth | 604/385.2 |
| 3,400,718 | 9/1968 | Saijo . | |
| 4,381,781 | 5/1983 | Sciaraffa et al. | 604/372 |
| 4,834,740 | 5/1989 | Suzuki et al. | 604/385.2 |
| 4,940,464 | 7/1990 | Van Gompel et al. | 604/385.2 |
| 4,988,346 | 1/1991 | Pfefferkorn | 604/389 |
| 5,061,261 | 10/1991 | Suzuki et al. | 604/385.2 |
| 5,069,678 | 12/1991 | Yonamoto et al. | 604/385.1 |
| 5,080,658 | 1/1992 | Igauz et al. | 604/385.2 |
| 5,137,526 | 8/1992 | Coates | 604/391 |
| 5,246,432 | 9/1993 | Suzuki et al. | 604/385.2 |
| 5,292,316 | 3/1994 | Suzuki | 604/358 |
| 5,454,803 | 10/1995 | Sageser et al. | 604/385.2 |
| 5,507,895 | 4/1996 | Suekane | 604/385.1 |
| 5,584,828 | 12/1996 | Yanamoto et al. | 604/385.2 |

FOREIGN PATENT DOCUMENTS

| | | | |
|---|---|---|---|
| 433951A2 | 6/1991 | European Pat. Off. . | |
| 528282A2 | 2/1993 | European Pat. Off. . | |
| 532034A2 | 3/1993 | European Pat. Off. . | |
| 4121419 | 1/1993 | Germany | 604/385.1 |
| 2214057 | 1/1988 | United Kingdom . | |
| 4010952 | 5/1994 | WIPO | 604/385.2 |

*Primary Examiner*—Mark O. Polutta
*Attorney, Agent, or Firm*—Jeffrey B. Curtin; Thomas D. Wilhelm

[57] ABSTRACT

An absorbent article includes an absorbent core located between a bodyside liner and an outer cover. A leg cuff is mounted to a base structure of the absorbent article in the crotch portion thereof. The leg cuffs are partially stretched when attached to respective longitudinal side portions near the crotch portion of the absorbent article. An outboard edge of the leg cuffs is generally unattached to the base structure of the absorbent article and can be stretched beyond the length of that portion of the base structure along which the leg cuffs are mounted. The leg cuffs may be mounted at an angle of between 5 and 25 degrees with respect to the longitudinal axis. The leg cuffs extend outwardly toward the rear portion of the absorbent article and inwardly in the front portion when mounted at an angle.

51 Claims, 4 Drawing Sheets

ABSORBENT ARTICLE USING EXTENSIBLE LEG CUFFS

BACKGROUND OF THE INVENTION

1. Technical Field

This invention pertains to an absorbent article for containing exudates. Such absorbent articles generally utilize leg cuffs to help prevent leakage of body exudates.

2. Description of the Related Art

Absorbent articles such as infant diapers, training pants, adult incontinence products, and the like are well known. Such articles have achieved a wide acceptance due to their ability to receive and absorb body exudates. In order to provide comfort to a user and contain exudates, the prior art generally discloses the use of leg elastics along the longitudinal edges of the base structure, or containment flaps extending longitudinally of the absorbent article and spaced inwardly of the longitudinal edge.

For example, U.S. Pat. No. 3,400,718 to Saijo discloses a sanitary belt including strips (6) which are attached in the crotch area by stitching. These strips are attached to the diaper in a relaxed state. The strips 6 are stretchable in two directions. The device of Saijo comprises a reusable holder for feminine napkins.

U.S. Pat. No. 5,137,526 to Coates discloses isolation gussets (22) for controlling transverse leakage in a reusable infant or adult diaper. The gussets are attached in the crotch portion of the diaper.

These devices both attempt to prevent the leakage of exudates by the user thereof. Neither device discloses partially stretching the leg cuff when mounting the leg cuff onto the holder or diaper.

SUMMARY OF THE INVENTION

This invention relates to an absorbent article designed to absorb body exudates. The absorbent article includes an absorbent core located between a bodyside liner and an outer cover. Leg cuffs formed by strips of material are attached to the absorbent article in the crotch portion thereof. The leg cuffs can be placed at a particular angle and shaped to provide increased comfort and leakage protection for a user. The leg cuffs are also formed of a material which stretches to provide greater comfort to a user. The leg cuffs are partially stretched when the inboard edges of the leg cuffs are mounted to the absorbent article. This partial stretching allows the leg cuff to gather the base structure of the absorbent article, thus providing a comfortable nongapping or snug fit for users with small legs. The outboard edge of the leg cuff thus can stretch a distance greater than the length of the inboard edge of the leg cuff. Therefore, the leg cuff can stretch beyond a length of the base structure along which the leg cuff is attached, to accommodate users with larger legs. Mounting the leg cuffs to the absorbent article at an angle of between about 5 degrees and about 25 degrees in combination with a narrow crotch width also prevents pull down of the front portion of the absorbent article. These arrangements increase the comfort for a user and also increase the sealing effect of the leg cuffs, with minimal distortion of the absorbent article.

Some of the objects of the invention are obtained in a first embodiment comprising an absorbent article having a front portion, a rear portion and a crotch portion connecting the front and rear portions, with a longitudinal axis extending through the front, rear and crotch portions, the absorbent article having opposing longitudinal sides with the longitudinal axis disposed therebetween, the absorbent article comprising an outer cover; a bodyside liner mounted to the outer cover, the outer cover and the bodyside liner forming, in combination, a base structure; an absorbent core located between the bodyside liner and the outer cover; and first and second extensible leg cuffs attached to the base structure along the respective opposing longitudinal sides of the absorbent article at the crotch portion, the leg cuffs being partially stretched when the base structure is fully extended; whereby the leg cuffs retract and gather the base structure in the crotch portion when the extensible leg cuffs are relaxed.

In most embodiments, the leg cuffs each have an outboard edge spaced outwardly from a respective lateral edge of the base structure and an Inboard edge mounted upon a respective portion of the base structure, each outboard edge preferably being attached at ends thereof to a respective portion of the base structure.

In some embodiments, the extensible leg cuffs are the entire source of elastic tension for the opposing longitudinal sides at the crotch portion of the absorbent article.

In other embodiments, the leg cuffs each have an outboard edge spaced outwardly from a lateral edge of the base structure, at least the respective outboard edges of the leg cuffs remaining further extensible when the base structure upon which the leg cuffs are mounted is fully extended. Further the entire surface of each of the leg cuffs that faces the base structure may be attached to the base structure at respective portions thereof.

In still other embodiments, each respective leg cuff has an unattached width thereof, between the base structure and the outboard edge of the respective leg cuff, of between about 0.1 inch and up to the full-width of the leg cuff piece. In part because of the lack of attachment, at least the outboard edges of the respective leg cuffs, spaced outwardly from a lateral edge of the base structure, are movable independent of the base structure of the absorbent article.

In yet other embodiments, the leg cuffs are stretched from about 5% to about 95%, and preferably 20% to 50%, of the total potential elongation of the leg cuffs, when the base structure is fully extended.

In another set of preferred embodiments, the leg cuffs have a maximum elongation of approximately 200% of the relaxed length of the leg cuffs. The leg cuffs are also approximately 1.5 inches wide and exert approximately 225 grams of restorative force at 90% elongation.

The invention further comprehends the leg cuffs having rectangular, elliptical or contoured shapes and a length to width ratio of between about 2:1 and about 20:1, preferably about 5:1 to about 15:1, most preferably about approximately 7:1. These length to width ratios are measured as attached to the diaper chassis.

In another embodiment, the leg cuffs comprise a laminate including first and second outer nonwoven facing layers on opposing sides of an elastomeric core layer, the elastomeric core layer comprising a thermoplastic elastomeric composition such as a styrene ethylene butylene styrene terpolymer. Further, the leg cuffs can be attached to the bodyside liner, as well as, or in addition to, the outer cover.

Other materials which may comprise the leg cuffs include: spandex/nonwoven laminates, elastomeric meltblowns, cross-machine direction stretchable materials made with stretchable nonwovens, stretchable foams and the like.

The invention further comprehends an absorbent article having a front portion, a rear portion and a crotch portion connecting the front and rear portions, with a longitudinal axis extending through the front, rear and crotch portions, the absorbent article having opposing longitudinal sides, with the longitudinal axis disposed therebetween, the absorbent article comprising an outer cover; a bodyside liner mounted to the outer cover, the outer cover and the bodyside liner forming, in combination, a base structure; an absorbent core located between the bodyside liner and the outer cover; and first and second extensible leg cuffs attached to the base structure along the respective opposing longitudinal sides of the absorbent article at the crotch portion, the leg cuffs each having an outboard edge spaced outwardly from a respective lateral edge of the base structure, and an inboard edge mounted upon the respective portion of the base structure; whereby each outboard edge is stretchable to a length greater than the length of the respective inboard edge and being retractable to a length less than the length of the respective inboard edge.

The invention also comprehends an absorbent article having a front portion, a rear portion and a crotch portion connecting the front and rear portions, a longitudinal axis extending through the front, rear and crotch portions, the absorbent article having opposing longitudinal sides, with the longitudinal axis disposed therebetween, the absorbent article comprising an outer cover; a bodyside liner mounted to the outer cover, the outer cover and the bodyside liner forming, in combination, a base structure; an absorbent core located between the bodyside liner and the outer cover; and first and second extensible leg cuffs attached to the base structure along the respective opposing longitudinal sides of the absorbent article at the crotch portion, the leg cuffs each being mounted at an angle between 5 degrees and 25 degrees with respect to the longitudinal axis, the apex of the angle being located toward the front portion of the absorbent article; whereby the absorbent article substantially conforms to the shape of the user's body when mounted thereon.

The invention further comprehends an absorbent article having a front portion, a rear portion and a crotch portion connecting the front and rear portions, with a longitudinal axis extending through the front, rear and crotch portions, the absorbent article having opposing longitudinal sides with the longitudinal axis disposed therebetween, the absorbent article comprising an outer cover; a bodyside liner mounted to the outer cover, the outer cover and bodyside liner forming, in combination, a base structure; an absorbent core located between the bodyside liner and outer cover; and first and second extensible leg cuffs attached to the base structure along respective opposing longitudinal sides of the absorbent article at the crotch portion, the leg cuffs being partially stretched when the base structure is fully extended, the leg cuffs being stretched a different length at an inboard edge which is mounted upon a respective portion of the base structure than a length at an outboard edge of the leg cuff, whereby the leg cuffs retract and gather the base structure in the crotch portion when the extensible leg cuffs are relaxed. The different length at an inboard edge can be smaller, but preferably is greater than the length at the outboard edge of the leg cuff. The different length at the inboard edge with respect to the outboard edge of each said leg cuff causes the leg cuffs to have a curved shape when attached to the base structure, even if the leg cuff comprises a rectangular shaped piece of material.

Figure 1:
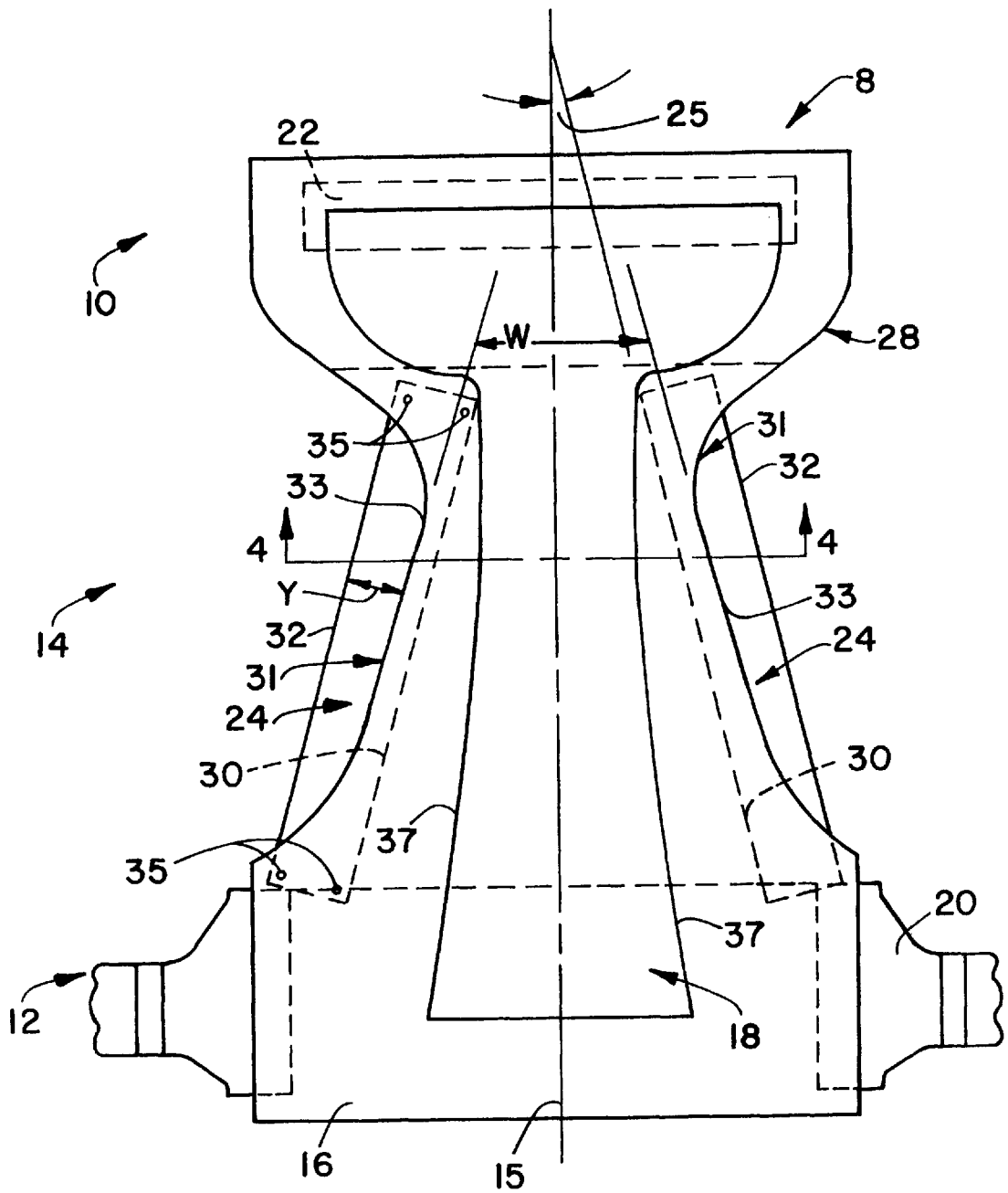
FIG. 1 illustrates a top view of an absorbent article according to the present invention with rectangular shaped leg cuffs.

The invention is not limited in its application to the details of construction and the arrangement of the components set forth in the following description or illustrated in the drawings. The invention is capable of other embodiments or of being practiced or carried out in various ways. Also, it is to be understood that the terminology and phraseology employed herein is for purpose of description and illustration and should not be regarded as limiting. Like reference numerals are used to indicate like components.

DETAILED DESCRIPTION OF THE PREFERRED EMBODIMENTS

The present invention relates to absorbent articles designed to absorb body exudates. While the preferred embodiments of the present invention are described herein in terms of an absorbent article such as a diaper for an infant, the invention includes, and is equally applicable to adult incontinent briefs, training pants and the like.

Figure 2:
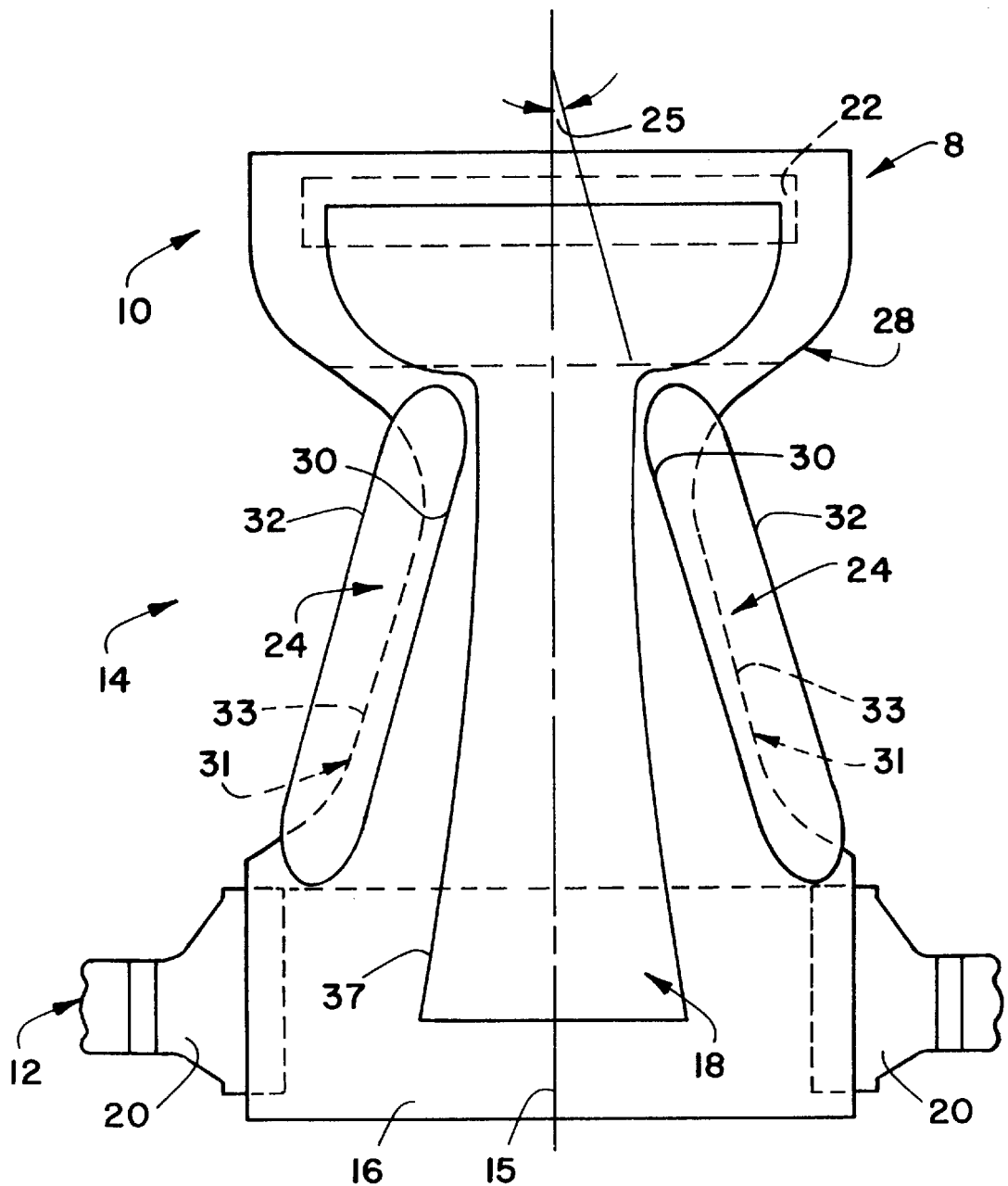
FIG. 2 illustrates a top view of another embodiment of the absorbent article with leg cuffs that have an elongated elliptical shape.
Figure 3:
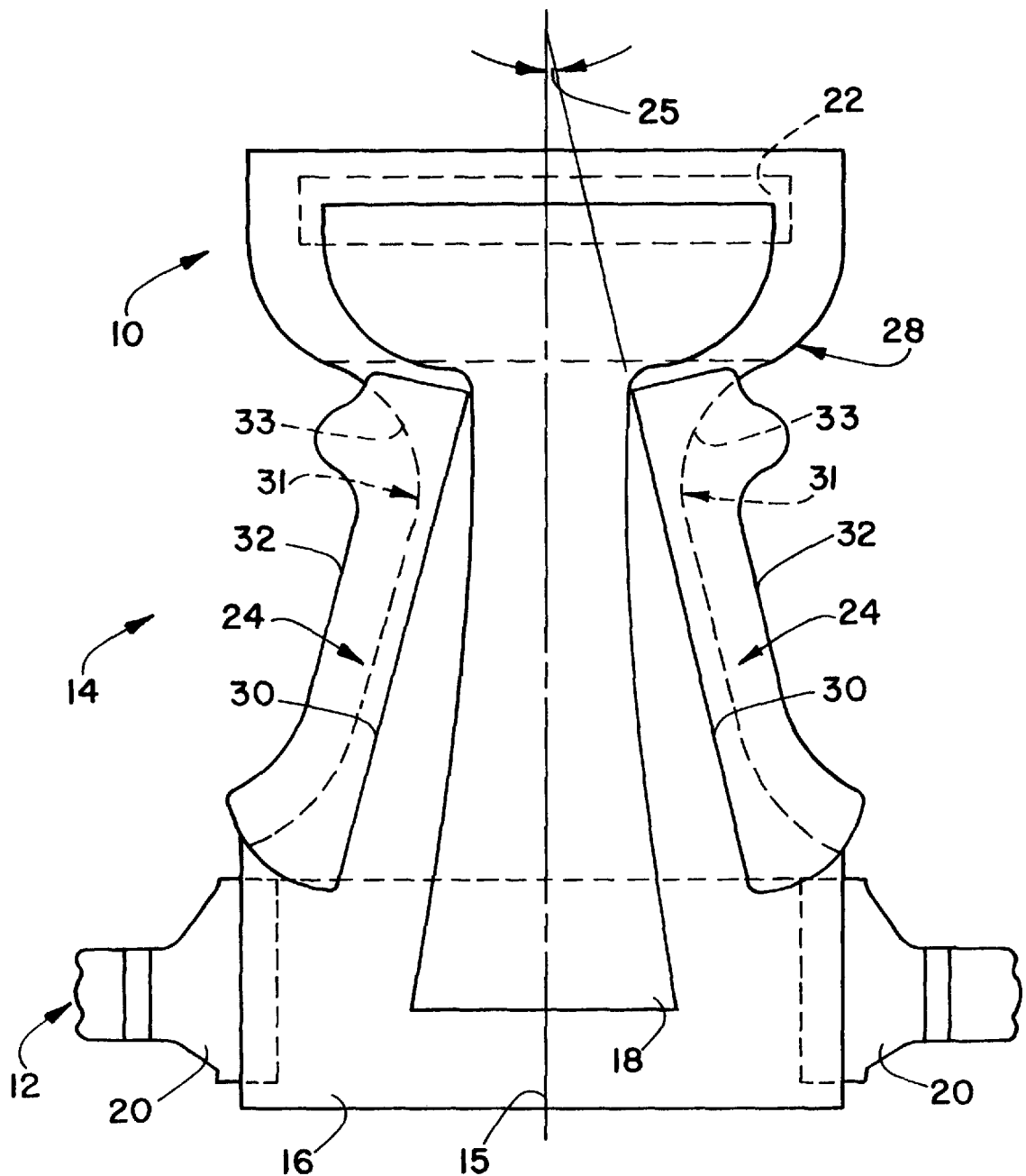
FIG. 3 illustrates a top view of yet another embodiment of the absorbent article including leg cuffs with a contoured shape.

The present invention can best be understood by reference to the drawings. FIG. 1 illustrates a top view of one embodiment of the invention where an absorbent article 8 comprises a front portion 10, a rear portion 12, and a crotch portion 14 located between and connecting the front portion 10 and the rear portion 12. A longitudinal axis 15 extends centrally through the front portion 10, the rear portion 12 and the crotch portion 14 of the absorbent article 8. The absorbent article 8 also includes a bodyside liner 16, an absorbent core 18, fasteners 20 on a rear portion 12 of the absorbent article 8, attachment means 22 on a front portion 10 of the absorbent article 8 and extensible leg cuffs 24 in the crotch portion 14 of the absorbent article 8 on opposing sides of longitudinal axis 15. The bodyside liner 16 and an outer cover 26 shown in FIGS. 4–6, in combination, form a base structure 28. An inboard edge 30 of the extensible leg cuff 24 is attached to the base structure 28 by heat sealing, sonic bonding, adhesive bonding or the like. The leg cuffs 24 span the length of the leg cut out or opening 31 in the crotch portion 14 of the absorbent article 8. Thus leg cuffs 24 are substantially confined to the crotch portion as shown in FIGS. 1–3. Adhesive bonding includes the use of glue lines, glue dots and/or other arrangements. An outboard edge 32 of the extensible leg cuff 24 may be attached by similar means at its ends to the base structure 28. The outboard edge 32 is spaced outwardly from a lateral edge 33 of the base structure 28 at least in the center region of the leg cuff 24. The base structure 28 preferably also has a relatively narrow width "W" which may be tapered as shown in FIG. 1, across the crotch portion 14.

The fasteners 20 can comprise a mechanical fastener such as the hook of a hook and loop fastening system mounted on outer cover 26 of base structure 28. The attachment means or other fastener surface 22 then comprises a corresponding loop material attached to the outer cover 26 and adapted to releasably engage with the hook material of the first fastener 20. Other well known fastening means can also be used to support the absorbent article 8 upon a person. For example, a cohesive system, an adhesive fastener system or the like may also be utilized to fasten the absorbent article 8.

Figure 6:
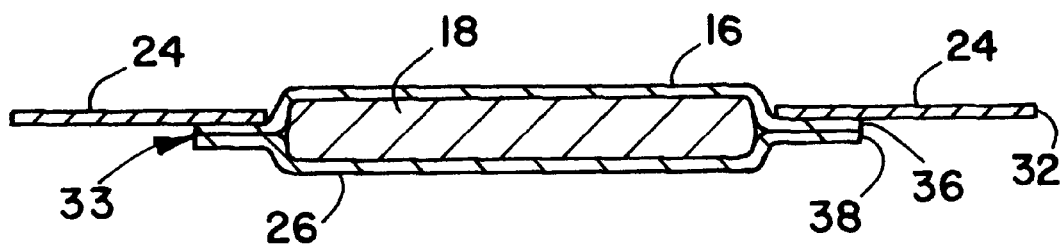
FIG. 6 illustrates a cross-sectional view as in FIG. 4 wherein the leg cuff is attached to the bodyside liner.

A suitable bodyside liner 16 may be manufactured from a wide selection of web materials, such as porous foams, reticulated foams, apertured plastic films or natural fibers. For example, the bodyside liner 16 may comprise wood or cotton fibers. Other possible materials are synthetic fibers, such as polyester or polypropylene fibers, or a combination of natural and synthetic fibers. Bodyside liner 16 is suitably utilized to help isolate the liquids held in the absorbent core 18 from the wearer's skin. As shown in FIGS. 1 6, bodyside liner 16 is free from any apertures which would enable solid exudates to pass therethrough. Thus bodyside liner 16 assists in enabling liquids to pass therethrough to absorbent core 18, while limiting the ability of solids, such as fecal material, to pass therethrough.

Various woven and nonwoven fabrics can be used for bodyside liner 16. For example, bodyside liner 16 may be composed of a meltblown or spunbonded web of polyolefin fibers. The bodyside liner 16 may also comprise a carded and/or bonded web composed of natural and/or synthetic fibers. The bodyside liner 16 may also be composed of a substantially hydrophobic material wherein the hydrophobic material is treated with a surfactant or otherwise processed to impart a desired level of wettability and hydrophilicity. In a particular embodiment of the present invention, the bodyside liner 16 may comprise a spunbonded polypropylene fabric composed of about 2.8–3.2 denier fibers formed into a web having a basis weight of about 22 grams per square meter and a density of about 0.06 grams per cubic centimeter. The fabric is treated with about 0.3 weight percent of a surfactant. The bodyside liner 16 may comprise a multiplicity of components, layers, or partial layers, which correspond to any of the materials disclosed herein, as well as others known in the art.

The absorbent core 18 suitably comprises a matrix of hydrophilic fibers, such as a web of cellulosic fluff, preferably in combination with a high-absorbency material commonly known as superabsorbent material. In a particular embodiment, absorbent core 18 comprises a mixture of superabsorbent hydrogel-forming particles and wood pulp fluff. In place of the wood pulp fluff, one may use synthetic, polymeric, meltblown fibers or a combination of meltblown fibers and natural fibers. The superabsorbent material may be substantially homogeneously mixed with the hydrophilic fibers or may be otherwise combined into the absorbent core.

Alternatively, the absorbent core 18 may comprise a laminate of fibrous webs and superabsorbent material or other suitable means of maintaining a superabsorbent material in a localized area.

The absorbent core 18 can have any of a number of shapes. For example, the absorbent core may be rectangular, T-shaped as shown in FIGS. 1–3 or I-shaped. It is generally preferred that the absorbent core 18 be narrower in the crotch portion 14 than the rear and/or front portions 12, 10.

The high-absorbency material in the absorbent core 18 can be selected from natural, synthetic and modified natural polymers and materials. The high absorbency materials can be inorganic materials, such as silica gels, or organic compounds, such as crosslinked polymers. The term crosslinked refers to any means for effectively rendering normally water-soluble materials substantially water insoluble but swellable, whereby absorbent properties are available but the swelled material is substantially immobile after absorbing water-based liquids. Such means can include, for example, physical entanglement, crystalline domains, covalent bonds, ionic complexes and associations, hydrophilic associations such as hydrogen bonding, and hydrophobic associations or Van der Waals forces.

It is generally preferred that the outer cover 26 of the absorbent article 8 be formed from a material which is substantially impermeable to liquids. A typical outer cover 26 may be manufactured from a thin plastic film or other flexible liquid-impermeable material. For example, the outer cover 26 can be formed by a polyethylene film having a thickness of from about 0.012 millimeters to about 0.051 millimeters. When it is desirable that the outer cover 26 have a more clothlike feeling, it may comprise a polyethylene film laminated to a surface of a nonwoven web, such as a spunbond web of polyolefin fibers. For example, a polyethylene film having a thickness of about 0.015 millimeters may have thermally or otherwise laminated thereto a spunbond web of polyolefin fibers having a thickness from 1.5 to 2.5 denier per filament, which nonwoven web has a basis weight of about 24 grams per square meter. Further, the outer cover 26 can be formed of a woven or nonwoven fibrous web which has been totally or partially constructed or treated to impart a desired level of liquid impermeability to selected regions that are adjacent or proximate the absorbent core 18. Still further, the outer cover 26 may optionally be composed of a micro-porous material which permits vapors to escape from the absorbent core 18 and through outer cover 26 while preventing liquid exudates from passing through the outer cover 26.

Figure 4:
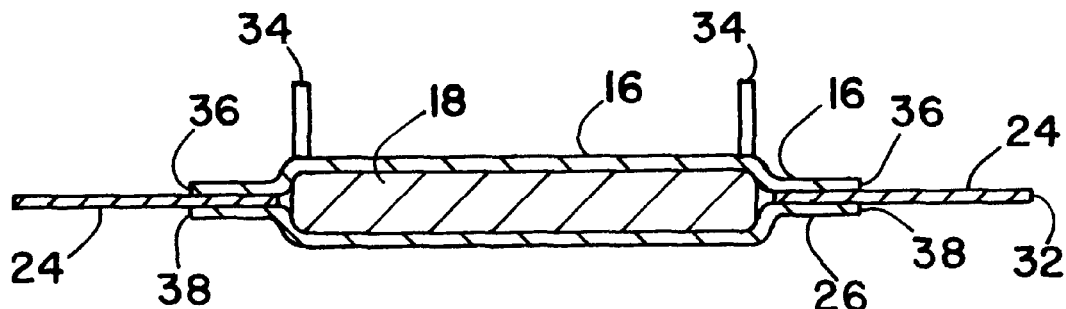
FIG. 4 illustrates a cross-sectional view taken at 4—4 of FIG. 1, showing attachment of the leg cuff to the bodyside liner and the outer cover.
Figure 5:
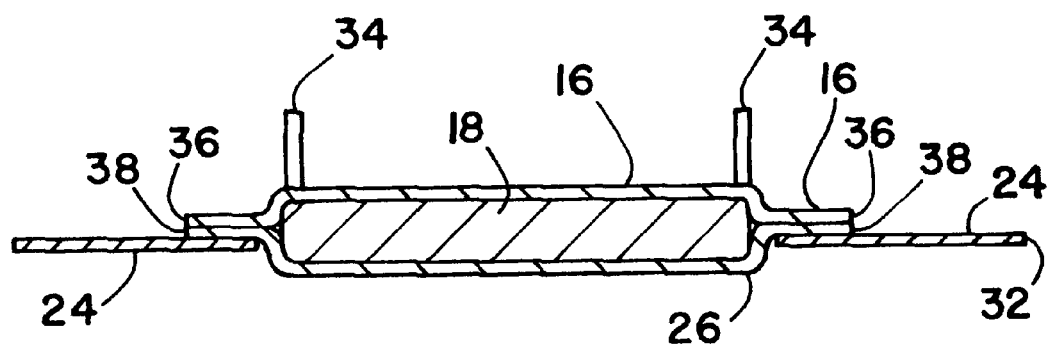
FIG. 5 illustrates a cross-sectional view as in FIG. 4 wherein the leg cuff is attached to the outer cover.

Optionally, inner containment flaps 34 shown in the cross-sectional views in FIGS. 4 and 5 may be utilized to contain exudates in the center of the crotch portion 14 of the absorbent article 8. Containment flaps 34, in combination with the extensible leg cuffs 24, provide enhanced protection against leakage of exudates from the absorbent article 8, because exudates must pass around two barriers in order to leak out of the absorbent article 8 in a lateral direction in the crotch portion 14. First, exudates must pass around the respective containment flap 34. Then the exudates must also pass around the respective leg cuffs 24. The containment flaps 34 impede flow of exudates to leg cuffs 24, such that the quantity of exudates reaching leg cuffs 24 is reduced according to the amount retained by containment flaps 34. The leg cuffs 24 more effectively impede flow of this reduced quantity of exudates, whereby the potential for transverse leakage of exudates past the leg cuffs 24 is reduced by the operation of containment flaps 34 at loci disposed inwardly of the leg cuffs 24.

The containment flaps 34 are preferably mounted upon the bodyside liner 16 e.g. near, or at the longitudinal edges, of the absorbent core 18 in a substantially parallel orientation with respect to the longitudinal axis 15 as illustrated in FIGS. 4 and 5, or may, for example, be mounted substantially parallel the side edges 37 of absorbent core 10 or side edges of the base structure 28, along the length of the crotch portion 14, maintaining straight-line extensions of that orientation across front and rear portions 10, 12.

The containment flaps 34 are preferably mounted on the bodyside liner 16 outwardly spaced from the absorbent core 18 and inwardly spaced from the leg cuffs 24. The containment flaps 34 can run the entire length of the absorbent article 8 through the front portion 10, crotch portion 14 and the rear portion 12. In the alternative, the containment flaps 34 can be present only in the crotch portion 14 of the absorbent article, or in the crotch portion 14 and part of one or both of the front portion 10 and rear portion 12.

The containment flaps 34 may include flap elastics (not shown) which comprise, for example, one or more individual strands of elastomeric material. A suitable elastic strand may, for example, be composed of a 470 decitex LYCRA® elastomer or other elastomers with suitable characteristics. The containment flaps 34 may comprise any flap configuration or design well known in the art.

The containment flaps 34 may be constructed of a material which is the same as, or different than the material comprising bodyside liner 16. Alternatively, the containment flaps 34 may comprise a material which is the same as the material used in outer cover 26. The containment flaps 34 are preferably liquid impervious. The containment flaps 34 may be formed from a polymeric film material or from e.g. a nonwoven material which has been treated so as to be substantially liquid impervious. The containment flaps 34 may be formed by a single or multiple layer of material with appropriate elastics secured thereto. Other arrangements are also contemplated. For example, the elastics may be placed at multiple spaced locations on the containment flap 34.

Each extensible leg cuff 24 is preferably formed of a separate length of material which is subsequently attached to the base structure 28. As shown in the cross-sectional view of FIG. 4, the extensible leg cuff 24 can be bonded or otherwise attached to outer cover 26 and bodyside liner 16 between facing surfaces of outer cover 26 and bodyside liner 16, over an area extending from an outer lateral edge 36 of the bodyside liner 16 and an outer lateral edge 38 of the outer cover 26, in the crotch portion 14 of the absorbent article 8, generally to the inboard edge 30 of the leg cuff 24. The combination of attachment to both the bodyside liner 16 and the outer cover 26 constitutes attachment to the base structure 28 because the base structure 28 is formed by both the bodyside liner 16 and the outer cover 26.

The extensible leg cuff 24 can, in the alternative, be adhesively bonded or otherwise attached only to the outer cover 26 of the base structure 28 as shown in the cross-sectional view of FIG. 5. Further, as illustrated in the cross-sectional view of FIG. 6, the leg cuffs 24 can also be attached only to the bodyside liner 16 of the base structure 28.

In all of the arrangements illustrated, at least part of the leg cuff 24 is spaced outwardly from a lateral edge 33 of the base structure 28. The lateral edge 33 of the base structure 28 comprises at least one of the outer lateral edge 36 of the bodyside liner 16 and the outer lateral edge 38 of the outer cover 26.

The leg cuff 24 can be bonded or attached to the base structure 28 by any suitable web attachment means, such as the use of adhesives, ultrasonic bonding or a combination thereof. Other possible attachment methods include stitching, plastic welding, solvent bonding and the like. Preferably, the entire portion of the surface of the leg cuff 24 which faces the base structure 28 is attached to the base structure 28. FIG. 1 illustrates ultrasonic bonds 35. The ultrasonic bonds enhance the securement of the leg cuffs 24 upon the base structure 28. These ultrasonic bonds are placed in each of the respective corners of the elongated rectangular shaped leg cuff to supplement the bonds at other portions of the leg cuff 24 already attached to the base structure 28 as shown in FIG. 1.

Figure 7:
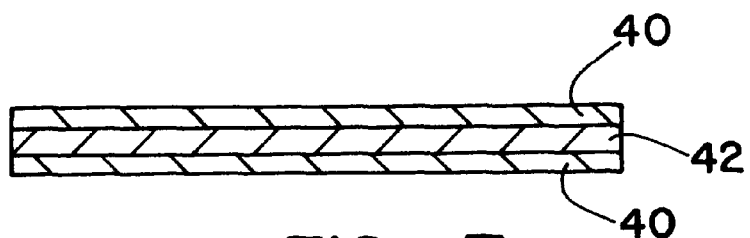
FIG. 7 shows one embodiment of the materials comprising the respective leg cuffs.

The preferred material for the leg cuffs 24 is a laminate of an elastomeric core layer 42 with bicomponent spunbonded facing layers 40 on opposite sides of the elastomeric core layer. The elastomeric core layer 42 preferably comprises a styrene ethylene butylene styrene terpolyer, such as a KRATON® G polymer from Shell Chemical Company. As shown in FIG. 7, the elastomeric core layer 42 which comprises a barrier to fluid is placed between spunbonded facing layers 40 to form a 3-layer stretchbonded laminate. While a terpolymer is preferred, other polymers such as copolymers can also provide an elastomeric core layer with similar properties.

As used herein, a stretch-bonded laminates is a multiple layer structure comprised of at least a two layers in which one layer is a gatherable layer and the other layer a stretchable layer. The layers are joined together when the stretchable layer is in a stretched condition so that, upon relaxing the layers, the gatherable layer is gathered by the retractile forces exerted by the stretchable/stretched layer. The stretchable layer can be a film of stretchable material or a plurality of strands of a stretchable material. The extensible leg cuffs 24 of the invention are preferably stretchable only in the lengthwise direction. In the alternative, the leg cuffs 24 may be stretchable in both the lengthwise and crosswidth directions. Other materials, which can form the middle or elastomeric core layer 42, include an elastomeric material or a stretchable meltblown material which is a barrier to fluid. For example, a carded web may comprise the elastomeric core layer 42. Other materials which may comprise the leg cuffs 24 include neck-bonded laminates, or the like. The material forming the leg cuff 24 typically has a maximum elongation of about approximately 200% of the relaxed length of the leg cuff 24. The material forming the leg cuffs also has a cross-directional stiffness in the range of 50 to 1,100 milligrams as measured on a Gurley bending stiffness tester according to TAPPI test number T543om-94. The preferred cross-directional stiffness is at least 300 milligrams.

The extensible leg cuffs 24 preferably are bonded to the base structure 28 of the absorbent article 8 while partially stretched in a direction extending along the length of the leg cuff 24. The leg cuffs 24 are stretched from 5% to 95% of their total potential elongation and are attached to the base structure 28 in such partially stretched condition, with the base structure extended preferably to its stretching limit. At minimum, the percent elongation of a leg cuff 24 at attachment to the base structure 28 is greater than the percent elongation of the base structure 28 at the respective facing surfaces of base structure 28 and leg cuff 24.

The inboard edge 30 of the leg cuff 24 can also be stretched a different length than the outboard edge 32 of the leg cuff. In this instance, the length at the inboard edge 30 can be smaller, but preferably is greater than the length at the outboard edge 32 of the leg cuff 24. Such an arrangement means that the inboard edge 30 is stretched with a greater force than the outboard edge 32 of the leg cuff 24. Another effect of stretching the inboard edge 30 a different length than the outboard edge 32 is that the leg cuff 24 has a curved shape when attached to the base structure 28, even if the leg cuff 24 comprises a rectangular shaped piece of material. This arrangement can be used with contoured, elliptical or otherwise shaped leg cuffs 24 as well as a rectangular shaped leg cuff 24. This arrangement substantially conforms the leg cuff 24 to a user's body in the leg cut out opening 31.

Preferably, the leg cuffs 24 are stretched between 50% and 80% of the total potential elongation of the leg cuffs 24 when attached to the base structure 28 which is fully extended. In one embodiment, the leg cuffs are 1.5 inches wide and exert approximately 225 grams of retractile force at 90% ultimate elongation. The partial stretching of the leg cuff 24 before mounting the leg cuff 24 to the base structure 28 allows the outboard edge 32 of the leg cuff 24 to be subsequently stretched, after the leg cuff 24 is mounted to the base structure 28, to a length greater than the length of the respective inboard edge 30 which is attached to the base structure 28 and effectively unable to stretch beyond the length of that portion of the base structure 28 along which the leg cuffs 24 are mounted. The partial stretching of the leg cuff 24 also allows the outboard edge 32 to retract to a length less than the length of the inboard edge 30 when the leg cuff 24 is relaxed. This ability to retract when relaxed allows the extensible leg cuffs 24 to gather the base structure 28 in the crotch portion 14 and better fit users with small legs. The ability to stretch the outboard edge 32 of the leg cuffs 24 beyond the length of the inboard edge 30 allows for a more comfortable fit for a user with large legs. Accordingly, for a given size (e.g. length, width, area, etc.) of base structure 28, the enhanced expansion and contraction capabilities of leg cuffs 24, relative to the relatively less expansible base structure, provides a relatively wider range of sizes of users/people on which an absorbent article of the given size can readily be used.

Preferably, the extensible leg cuffs 24 also provide the entire source of retractile force for the opposing longitudinal sides of the crotch portion 14 of the absorbent article 8.

For a rectangular or like configuration, the size of the extensible leg cuffs 24 can be described in terms of a ratio of the length with respect to the width of the leg cuff 24. These length to width ratios are measured when the leg cuffs 24 are attached to the diaper chassis. The leg cuffs 24 generally have a length to width ratio of between about 2:1 and about 20:1. Preferably, the length to width ratio is between about 5:1 and about 15:1, most preferably approximately 7:1. The preferred width for the leg cuff 24 is approximately 1.5 inches. When the leg cuffs are mounted to the base structure 28, the leg cuffs 24 typically have an unattached width "Y" shown in FIG. 1 between the base structure 28 and the outboard edge 32 of between about 0.1 inch and 1.5 inches (up to the full-width of the leg cuff piece). The preferred unattached width is 1 inch. This unattached width, which is present at least in the center region of the leg cuffs 24, causes the leg cuffs 24 to operate and move with respect to a surface generally defined by base structure 28, substantially independently of the base structure 28 and responsive to only modest exertions of force, such as retractile forces of the leg cuffs 24 against the user's legs. This independent movement accompanied by the modest forces exerted on the user's legs, greatly increases the comfort of the leg cuffs 24 for a user's legs while maintaining a good barrier against transverse leakage of exudates past the leg cuffs 24.

FIGS. 1–3 show extensible leg cuffs 24 attached to the base structure 28 of the absorbent article 8 at a preferred angle 25 of 15 degrees with respect to the longitudinal axis 15. The apex of the angle 25 is located frontwardly towards the front portion 10 of the absorbent article 8 as shown in FIGS. 1–3. While an angle 25 of between 0 degrees and 30 degrees is considered effective for applicants' invention, a range for the angle 25 of approximately 5 degrees to 25 degrees is considered the preferred range for placement of the leg cuff 24.

Due to (i) the mounting angle 25 of the leg cuff 24, (ii) the position of the outboard edges 32 of the leg cuff 24 outwardly from the lateral edge 33 of the base structure 28, and (iii) the soft stretchable material which forms the leg cuff 24, desired properties are conferred to the absorbent article 8. For instance, the angle 25 and the relatively narrow crotch width, in combination, attenuate the tendency of the front portion 10 of the absorbent article 8 to be pulled downward in response to movement of the user's legs. The angle 25 also improves the buttocks coverage by conforming the absorbent article 8 more closely to the shape of a user's body. The above factors all improve the ability of the absorbent article 8 to provide a comfortable and effective seal of the user's legs. The preferred outward spacing of the outboard edge 32 of the leg cuffs 24 from the lateral edges 33 of the base structure 28 also allow one to reduce the width of the crotch e.g. between lateral edges 33, whereby lateral edges 33 play no direct role in forming a seal about the user's legs. Rather such seal is formed by leg cuffs 24. Accordingly, at least the outboard edges 32 of the leg cuffs 24 operate and move independently of the base structure 28. This attachment arrangement also allows the outboard edges 32 of the leg cuffs 24 to achieve a unique compound curvature due to minimizing the anti-gathering influence of the base structure 28 of the absorbent article 8 at outboard edges 32.

FIGS. 1–3 show exemplary shapes for the leg cuffs 24. FIG. 1 shows a typical rectangular shape for the leg cuffs 24. This shape is relatively easy to attach and glue to an absorbent article 8 during a construction process. FIG. 2 shows a typical elliptical pattern for the leg cuff 24. FIG. 3 shows an exemplary contoured pattern for the leg cuff 24 which may be customized or altered in any desired manner to fit a particular type of user or absorbent article 8. For example, the leg cuff 24 can comprise a curved shape where both the outboard edge 32 and the inboard edge 30 of the leg cuff 24 are curved with different or the same radii and substantially tailored to the shape of the leg cut out 31.

Those skilled in the art will now see that certain modifications can be made to the invention herein disclosed with respect to the illustrated embodiments, without departing from the spirit of the instant invention. And while the invention has been described above with respect to the preferred embodiments, it will be understood that the invention is adapted to numerous rearrangements, modifications, and alterations, and all such arrangements, modifications, and alterations are intended to be within the scope of the appended claims.

What is claimed is:

1. An absorbent article having a front portion and a rear portion, and a crotch portion connecting said front and rear portions, a longitudinal axis extending through said front, rear and crotch portions, said absorbent article having opposing longitudinal sides, with said longitudinal axis disposed therebetween, said absorbent article comprising:

(a) an outer cover;

(b) a bodyside liner mounted to said outer cover, said outer cover and said bodyside liner forming, in combination, a base structure;

(c) an absorbent core located between said bodyside liner and said outer cover; and (d) first and second extensible leg cuffs attached to said base structure at attachment loci along the respective opposing longitudinal sides of said absorbent article at said crotch portion, said leg cuffs being partially stretched when said base structure is fully extended, each said leg cuff having an inboard edge mounted on a respective portion of said base structure and extending outwardly to an outboard edge spaced outwardly from a respective lateral edge of said base structure each said outboard edge being attached to said base structure at an end thereof;

whereby said leg cuffs retract and gather said base structure in said crotch portion when said extensible leg cuffs are relaxed, and whereby when said base structure is fully extended, said leg cuffs can be further stretched at said outboard edges, such that the outboard edges are stretchable to lengths greater than the lengths of the respsective inboard edges and retract to lengths less than the lengths of the respective inboard edges.

2. The absorbent article of claim 1, said leg cuffs extending outwardly from said attachment loci in a constantly outward direction to the respective said outboard edges.

3. The absorbent article of claim 1, said leg cuffs being substantially confined to said crotch portion of said absorbent article.

4. The absorbent article of claim 1, at least said outboard edges of the respective said leg cuffs being movable independent of said base structure of said absorbent article.

5. The absorbent article of claim 1, said leg cuffs having facing surfaces thereof, and portions of such facing surfaces facing said base structure, said leg cuffs being attached to said base structure over the entireties of said facing portions.

6. The absorbent article of claim 1, each respective said leg cuff having an unattached width thereof, between the respective said lateral edge of said base structure and said outboard edge of the respective said leg cuff, of between about 0.1 inch and 1.5 inches.

7. The absorbent article of claim 1 wherein said leg cuffs are stretched from 5% to 95% of a total potential elongation of said leg cuffs when said base structure is fully extended.

8. The absorbent article of claim 7 wherein said leg cuffs are stretched between 50% and 80%, of the total potential elongation of said leg cuffs, when said base structure is fully extended.

9. The absorbent article of claim 1 wherein said leg cuffs have a maximum elongation of approximately 200% of the relaxed length of said leg cuffs.

10. The absorbent article of claim 9 wherein said leg cuffs are approximately 1.5 inches wide and exert approximately 225 grams of retractile force at 90% ultimate elongation.

11. The absorbent article of claim 1 wherein said leg cuffs have a rectangular shape.

12. The absorbent article of claim 1 wherein said leg cuffs have an elliptical shape.

13. The absorbent article of claim 1 wherein said leg cuffs have a contoured shape.

14. The absorbent article of claim 1 wherein said leg cuffs have a length to width ratio between 2:1 and 20:1.

15. The absorbent article of claim 1 wherein said leg cuffs have a length to width ratio of between 5:1 and 15:1.

16. The absorbent article of claim 1 wherein said leg cuffs have a length to width ratio of approximately 7:1.

17. The absorbent article of claim 1 wherein said leg cuffs comprise a laminate including first and second outer nonwoven facing layers on opposing sides of an elastomeric core layer.

18. The absorbent article of claim 17 wherein said elastomeric core layer comprises a styrene ethylene butylene styrene terpolymer.

19. The absorbent article of claim 1 wherein said leg cuffs are attached to said bodyside liner.

20. The absorbent article of claim 1 wherein said extensible leg cuffs represent the entirety of retractile forces operative in the longitudinal direction at longitudinal sides of said crotch portion.

21. The absorbent article of claim 1 wherein containment flaps are mounted upon said bodyside liner along each of the opposing longitudinal sides at said crotch portion in a substantially parallel direction with respect to said longitudinal axis, said containment flaps being spaced inwardly from said leg cuffs.

22. An absorbent article having a front portion and a rear portion, and a crotch portion connecting said front and rear portions, a longitudinal axis extending through said front, rear and crotch portions, said absorbent article having opposing longitudinal sides, with said longitudinal axis disposed therebetween, said absorbent article comprising:

(a) an outer cover;
(b) a bodyside liner mounted to said outer cover, said outer cover and said bodyside liner forming, in combination, a base structure;
(c) an absorbent core located between said bodyside liner and said outer cover;
(d) first and second extensible leg cuffs attached to said base structure along the respective opposing longitudinal sides of said absorbent article at said crotch portion, said leg cuffs each having an inboard edge mounted upon a respective portion of said base structure, said leg cuffs extending from the inboard edge outwardly to an outboard edge spaced outwardly from the respective lateral edge of said base structure, said leg cuffs being operatively confined to said crotch portion; and
(e) a fastener mounted to said base structure, securing said absorbent article to the body of a user;

whereby said leg cuffs stretch and retract in said crotch portion independently of any respective stretching and retracting of said base structure, such that outboard edges of said absorbent article are defined by said leg cuffs in said front and rear portions.

23. The absorbent article of claim 22 wherein said extensible leg cuffs represent the entirety of retractile forces operative in the longitudinal direction at longitudinal sides of said crotch portion.

24. The absorbent article of claim 22, said leg cuffs having facing surfaces thereof, and portions of such facing surfaces facing said base structure, said leg cuffs being attached to said base structure over the entireties of said facing portions.

25. The absorbent article of claim 22 wherein said leg cuffs are stretched from 50% to 80% of a total potential elongation of said leg cuffs, when said base structure is fully extended.

26. The absorbent article of claim 22 wherein said leg cuffs have a length to width ratio between 2:1 and 20:1.

27. The absorbent article of claim 22 wherein said leg cuffs comprise a laminate including first and second outer spunbonded facing layers on opposing sides of an elastomeric core layer.

28. The absorbent article of claim 27 wherein said elastomeric core layer comprises a styrene ethylene butylene styrene terpolymer.

29. The absorbent article of claim 22 wherein containment flaps are mounted upon said bodyside liner along each of the opposing longitudinal sides of said absorbent article at said crotch portion in a substantially parallel direction with respect to said longitudinal axis, said containment flaps being spaced inwardly from said leg cuffs.

30. An absorbent article having a front portion and a rear portion, and a crotch portion connecting said front and rear portions, a longitudinal axis extending through said front, rear and crotch portions, said absorbent article having opposing longitudinal sides, with said longitudinal axis disposed therebetween, said absorbent article comprising:

(a) an outer cover;
(b) a bodyside liner mounted to said outer cover, said outer cover and said bodyside liner forming, in combination, a base structure having a relatively narrow crotch width;

(c) an absorbent core located between said bodyside liner and said outer cover; and (d) first and second extensible leg cuffs attached to said base structure along the respective opposing longitudinal sides of said absorbent article at said crotch portion, said leg cuffs being operatively confined to said crotch portion, each said leg cuff having an outboard edge spaced outwardly from a respective lateral edge of said base structure, said leg cuffs each being mounted such that rear ends thereof are disposed at angles between 5 degrees and 25 degrees from respective front ends thereof, with respect to said longitudinal axis, the apex of the angle being located toward said front portion of said absorbent article, the combination of angles and the relatively narrow crotch width being effective to attenuate tendency of the front portion to be pulled downward in response to movement of the user's legs.

31. The absorbent article of claim 30 wherein said leg cuffs each have an inboard edge mounted upon a respective portion of said base structure, each said outboard edge being attached at ends thereof to the respective said portion of said base structure outwardly of the respective inboard edge.

32. The absorbent article of claim 30, at least the respective said outboard edges of said leg cuffs remaining further extensible when said base structure upon which said leg cuffs are mounted is fully extended.

33. The absorbent article of claim 30, at least said outboard edges of the respective said leg cuffs being movable independent of said base structure of said absorbent article.

34. The absorbent article of claim 30, said leg cuffs having facing surfaces thereof, and portions of such facing surfaces facing said base structure, said leg cuffs being attached to said base structure over the entireties of said facing portions.

35. The absorbent article of claim 30 wherein said leg cuffs are stretched from 50% to 80% of a total potential elongation of said leg cuffs when said base structure is fully extended.

36. The absorbent article of claim 30 wherein said leg cuffs have a rectangular shape.

37. The absorbent article of claim 30 wherein said leg cuffs have an elliptical shape.

38. The absorbent article of claim 30 wherein said leg cuffs have a contoured shape.

39. The absorbent article of claim 30 wherein said leg cuffs have a length to width ratio between 2:1 and 20:1.

40. The absorbent article of claim 30, wherein said leg cuffs are formed by a laminate including first and second outer spunbonded facing layers on opposing sides of an elastomeric core layer.

41. The absorbent article of claim 40 wherein said elastomeric core layer comprises a styrene ethylene butylene styrene terpolymer.

42. The absorbent article of claim 30 wherein said extensible leg cuffs represent the entirety of retractile forces operative in the longitudinal direction at longitudinal sides of said crotch portion.

43. The absorbent article of claim 30 wherein when each said inboard edge is mounted upon a respective portion of said base structure, and wherein, when said base structure is fully extended, each said outboard edge is stretchable to a length greater than the respective mounted length of said inboard edge and is retractable to a length less than the respective mounted length of said inboard edge.

44. The absorbent article of claim 30 wherein containment flaps are mounted upon said bodyside liner along each of the opposing longitudinal sides at said crotch portion in a substantially parallel direction with respect to said longitudinal axis, said containment flaps being spaced inwardly from said leg cuffs.

45. An absorbent article having a front portion and a rear portion, and a crotch portion connecting said front and rear portions, a longitudinal axis extending through said front, rear and crotch portions, said absorbent article having opposing longitudinal sides, with said longitudinal axis disposed therebetween, said absorbent article comprising:

(a) an outer cover;

(b) a bodyside liner mounted to said outer cover, said outer cover and said bodyside liner forming, in combination, a base structure;

(c) an absorbent core located between said bodyside liner and said outer cover; and (d) first and second extensible leg cuffs attached to said base structure along the respective opposing longitudinal sides of said absorbent article at said crotch portion, said leg cuffs having outboard edges thereof spaced outwardly from respective lateral edges of said base structure, said leg cuffs being operatively confined to said crotch portion, said leg cuffs being partially stretched, between 50 percent and 80 percent of total potential elongation when said base structure is fully extended such that the outboard edges can stretch and flex when the base structure is fully extended;

the enhanced expansion and contraction capabilities of said partially stretched leg cuffs, relative to said base structure, providing a relatively wider range of sizes of users on which said absorbent article can readily be used.

46. The absorbent article of claim 45, said leg cuffs being stretched a different length at an inboard edge which is mounted upon a respective portion of said base structure than a length at said outboard edge of said leg cuff, wherein said different length of each respective said inboard edge with respect to each respective said outboard edge of each said leg cuff shapes each respective said leg cuff in a curved manner when attached to said base structure.

47. The absorbent article of claim 45, at least the respective said outboard edges of said leg cuffs remaining further extensible when said base structure upon which said leg cuffs are mounted is fully extended.

48. The absorbent article of claim 45 wherein each respective said leg cuff has an unattached width thereof, between the respective said lateral edge of said base structure and said outboard edge of the respective said leg cuff, of between about 0.1 inch and 1.5 inches.

49. The absorbent article of claim 45 wherein said leg cuffs comprise a laminate including first and second outer nonwoven facing layers on opposing sides of an elastomeric core.

50. An absorbent article having a front portion and a rear portion, and a crotch portion connecting said front and rear portions, a longitudinal axis extending through said front, rear and crotch portions, said absorbent article having opposing longitudinal sides, with said longitudinal axis disposed therebetween, said absorbent article comprising:

(a) an outer cover;

(b) a bodyside liner mounted to said outer cover, said outer cover and said bodyside liner forming, in combination, a base structure, said base structure including opposing leg cut outs in said crotch portion;

(c) an absorbent core located between said bodyside liner and said outer cover; and (d) first and second extensible leg cuffs attached to said base structure along the respective longitudinal sides of said absorbent article at said crotch portion, said leg cuffs spanning the length of said leg cut outs in said crotch portion of said absorbent article, and being partially stretched in the crotch portion when said base structure is fully extended, each said leg cuff having an outboard edge spaced outwardly from a respective lateral edge of said base structure at the respective said leg cut outs substantially straight portions of said leg cuffs spanning curvilinear lateral edge portions of said base structure in said crotch portion;

whereby said leg cuffs operate to extend the effective width of the base structure with material that retracts and expands independently of the base structure to which such leg cuffs are attached.

51. An absorbent article of claim 50, wherein each said leg cuff has an inboard edge mounted upon a respective portion of said base structure, each said outboard edge being attached at ends thereof to the respective said portion of said base structure.

* * * * *

UNITED STATES PATENT AND TRADEMARK OFFICE
CERTIFICATE OF CORRECTION

| | |
|---|---|
| PATENT NO. : 6,117,121 | |
| DATED : September 12, 2000 | |
| INVENTOR(S) : Michael J. Faulks, et al. | |

It is certified that error appears in the above-identified patent and that said Letters Patent is hereby corrected as shown below:

<u>Column 5,</u>
Line 14, delete "FIGS. 16" and insert -- FIGS. 1-6 --.

<u>Column 8,</u>
Line 8, delete "stretch-bonded laminates" and insert -- "stretch-bonded laminate" -- in place thereof.

<u>Claim,</u>
<u>Claim 21,</u>
Line 21, after "structure" insert -- , --;
Line 23, delete ";" and insert -- , -- in place thereof.

Signed and Sealed this

Sixth Day of November, 2001

*Attest:*

*Nicholas P. Godici*

*Attesting Officer*

NICHOLAS P. GODICI
*Acting Director of the United States Patent and Trademark Office*

UNITED STATES PATENT AND TRADEMARK OFFICE
CERTIFICATE OF CORRECTION

PATENT NO. : 6,117,121
DATED : September 12, 2000
INVENTOR(S) : Michael J. Faulks et al.

It is certified that error appears in the above-identified patent and that said Letters Patent is hereby corrected as shown below:

Column 5,
Line 14, delete "FIGS. 16" and insert -- FIGS. 1-6 --.

Column 8,
Line 8, delete "stretch-bonded laminates" and insert -- "stretch-bonded laminate" -- in place thereof.

Claim 1,
Line 21, after "structure" insert -- , --;
Line 23, delete ";" and insert -- , -- in place thereof.

This certificate supersedes Certificate of Correction issued November 6, 2001.

Signed and Sealed this

Nineteenth Day of February, 2002

Attest:

Attesting Officer

JAMES E. ROGAN
*Director of the United States Patent and Trademark Office*